United States Patent
Yamaguchi et al.

(10) Patent No.: US 8,585,586 B2
(45) Date of Patent: Nov. 19, 2013

(54) ELECTRONIC ENDOSCOPE SYSTEM, PROCESSOR FOR ELECTRONIC ENDOSCOPE, AND TARGET TRACING METHOD

(75) Inventors: Hiroshi Yamaguchi, Kanagawa (JP); Takayuki Iida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 113 days.

(21) Appl. No.: 13/108,086

(22) Filed: May 16, 2011

(65) Prior Publication Data

US 2011/0301443 A1 Dec. 8, 2011

(30) Foreign Application Priority Data

Jun. 8, 2010 (JP) ................................ 2010-130846

(51) Int. Cl.
*A61B 1/06* (2006.01)
*A61B 1/04* (2006.01)
*A61B 1/00* (2006.01)

(52) U.S. Cl.
USPC ........... 600/160; 600/109; 600/178; 600/101; 382/133

(58) Field of Classification Search
USPC ......... 600/160, 324, 109, 310, 473, 431, 476; 351/246, 208, 206; 382/133, 131, 128; 348/68, 65; 362/574
See application file for complete search history.

(56) References Cited

U.S. PATENT DOCUMENTS

| | | | |
|---|---|---|---|
| 2004/0010192 A1* | 1/2004 | Benaron et al. | 600/431 |
| 2004/0257438 A1* | 12/2004 | Doguchi et al. | 348/65 |
| 2007/0016077 A1* | 1/2007 | Nakaoka et al. | 600/476 |
| 2009/0023991 A1* | 1/2009 | Gono et al. | 600/109 |
| 2009/0082625 A1* | 3/2009 | Gono | 600/109 |
| 2009/0091614 A1* | 4/2009 | Gono et al. | 348/68 |
| 2009/0262225 A1* | 10/2009 | Yamaguchi et al. | 348/265 |
| 2010/0039507 A1* | 2/2010 | Imade | 348/68 |
| 2010/0106026 A1* | 4/2010 | Benaron et al. | 600/476 |
| 2010/0158330 A1* | 6/2010 | Guissin et al. | 382/128 |
| 2011/0319711 A1* | 12/2011 | Yamaguchi et al. | 600/109 |

FOREIGN PATENT DOCUMENTS

| | | |
|---|---|---|
| JP | 10-216080 | 8/1998 |
| JP | 10-323322 | 12/1998 |
| JP | 2000-262459 | 9/2000 |
| JP | 2002-95625 A | 4/2002 |
| JP | 2003-535659 A | 12/2003 |
| JP | 2010-094152 | 4/2010 |
| WO | WO 2007031946 A2 * | 3/2007 |

* cited by examiner

*Primary Examiner* — John P Leubecker
*Assistant Examiner* — Ronald D Colque
(74) *Attorney, Agent, or Firm* — Birch, Stewart, Kolasch & Birch, LLP

(57) ABSTRACT

In a tracing mode of an electronic endoscope system, a target designating frame is displayed on a monitor to enable designating a tracing target in an endoscopic image captured from an interior of a body cavity illuminated with a broadband light. After the tracing target is designated, narrowband rays of different wavelength ranges from each other are sequentially projected into the body cavity, to acquire biological information on the designated tracing target from image signals obtained under these narrowband rays. On the basis of the biological information on the tracing target, an area corresponding to the tracing target is detected from endoscopic images newly captured after the designation of the tracing target.

12 Claims, 14 Drawing Sheets

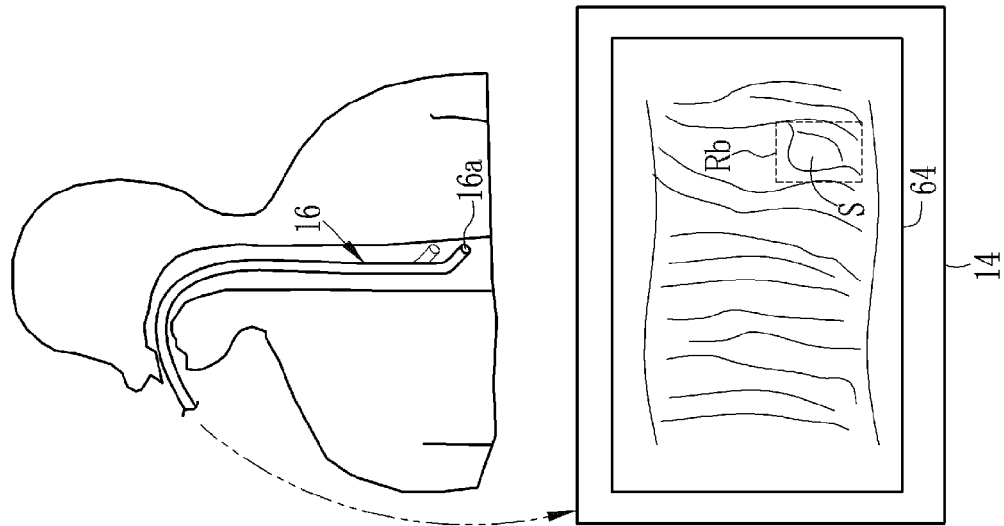
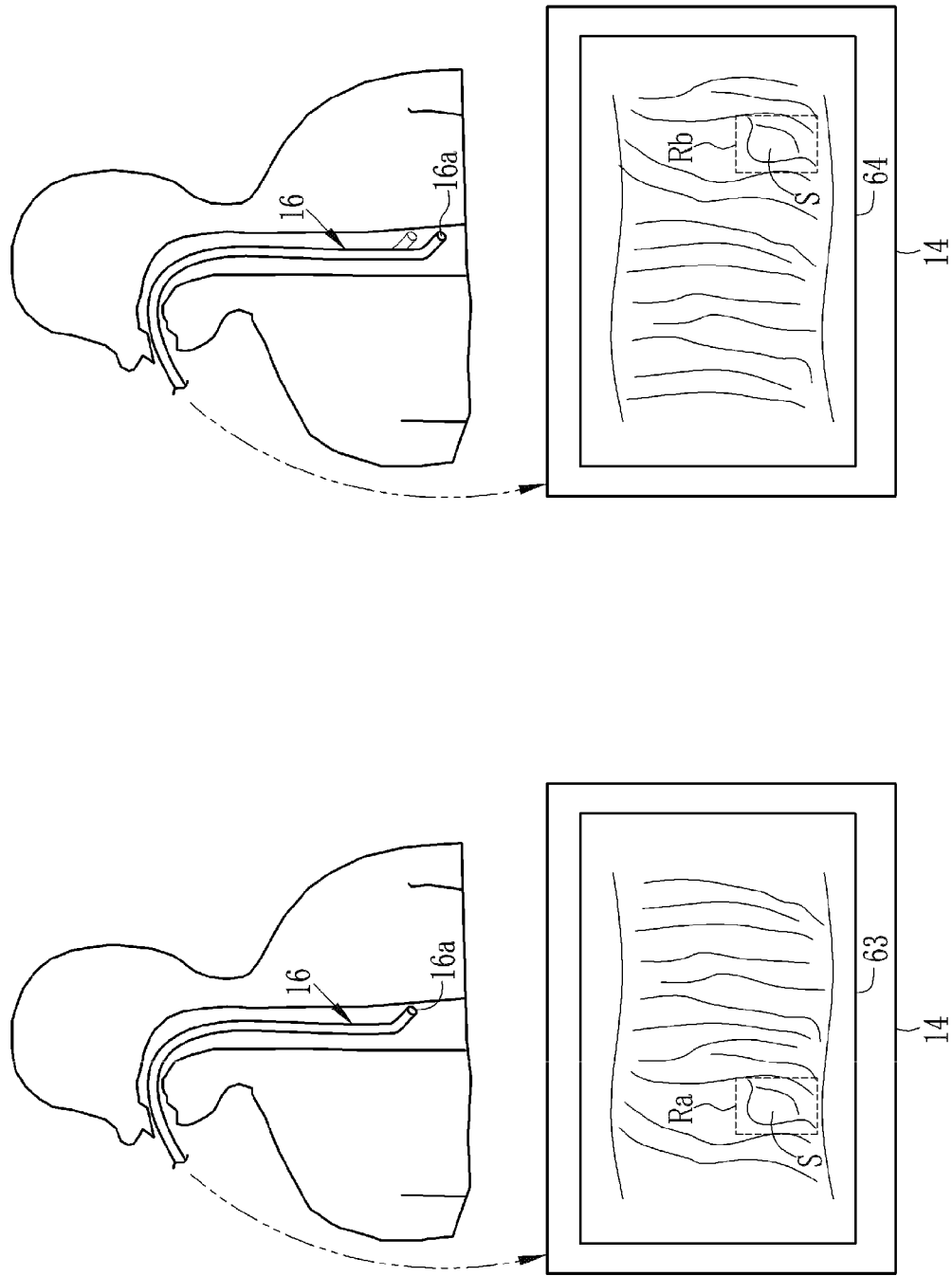

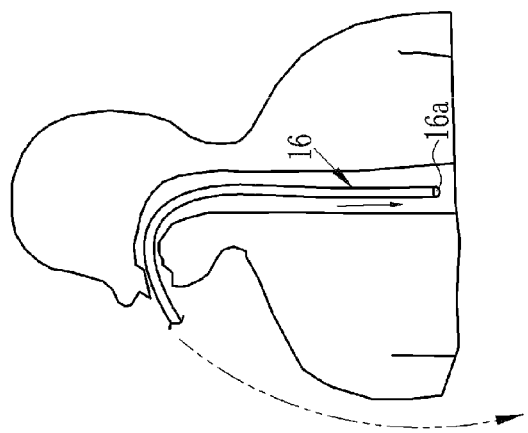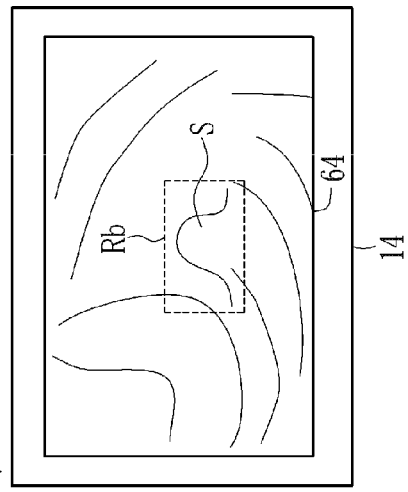
FIG.6A
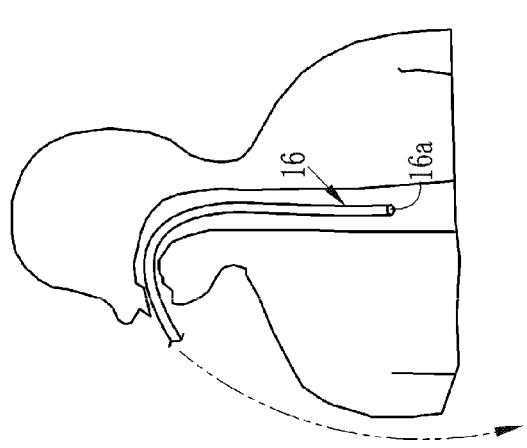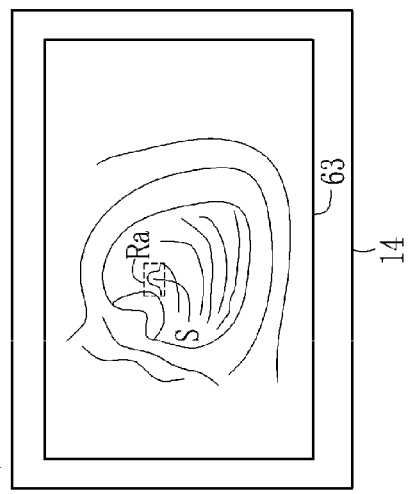
FIG.6B

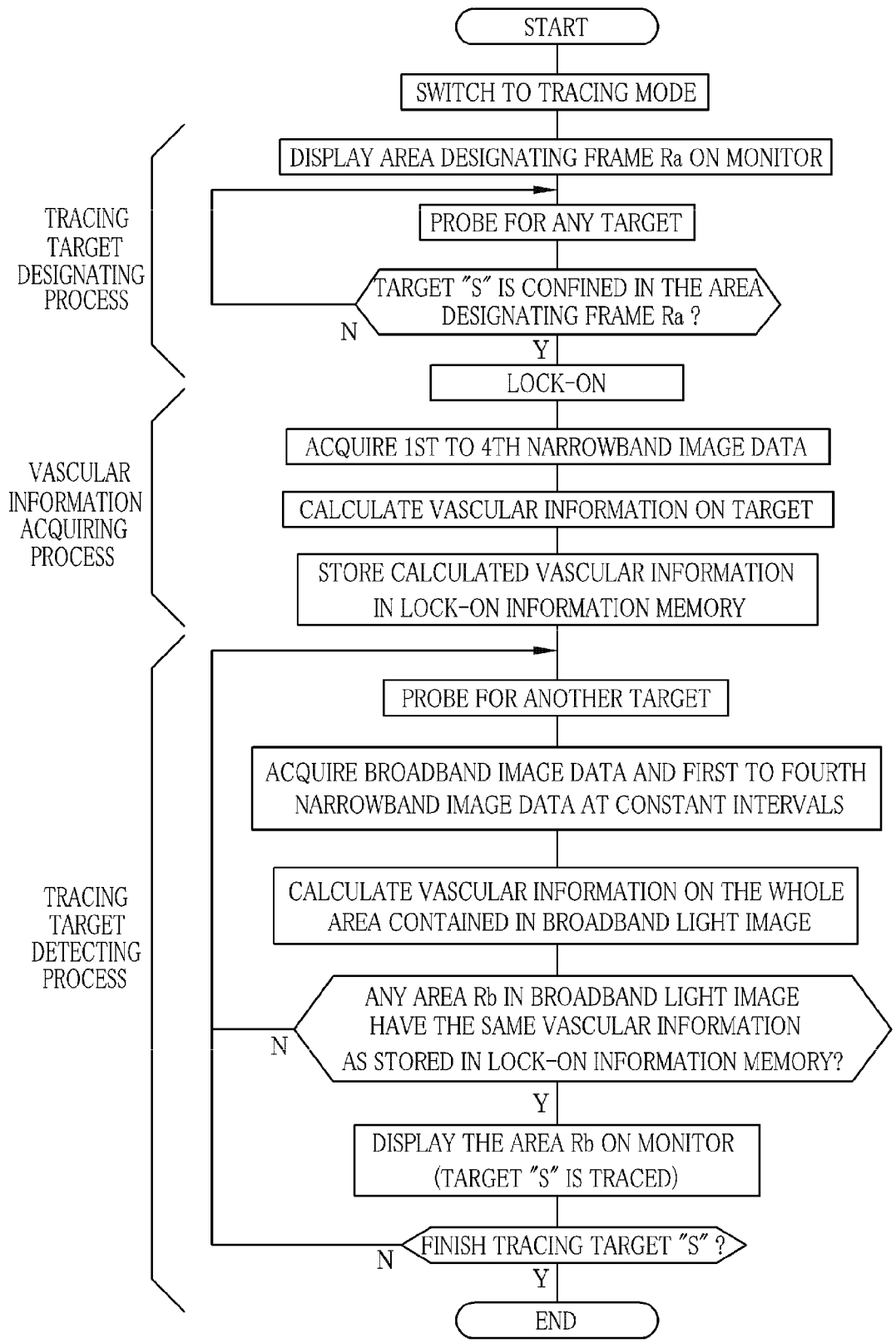

ELECTRONIC ENDOSCOPE SYSTEM, PROCESSOR FOR ELECTRONIC ENDOSCOPE, AND TARGET TRACING METHOD

FIELD OF THE INVENTION

The present invention relates to an electronic endoscope system for tracing a target such as a pathologic lesion based on images captured through an electronic endoscope. The present invention also relates to a processor for the electronic endoscope, and a target tracing method therefor.

BACKGROUND OF THE INVENTION

In recent medical field, electronic endoscopes are frequently used for diagnoses and treatments. The electronic endoscope has a probing portion that is inserted into a body cavity of a subject under inspection, and an imaging unit including a CCD or the like is incorporated in a distal end of the probing portion. The electronic endoscope is also connected to a light source unit, so that light from the light source unit is projected from the distal end of the probing portion to illuminate the inside of the body cavity. While the inside of the body cavity is being illuminated, subject tissues inside the body cavity are imaged by the imaging unit. Captured images are processed in various ways in a processor which is also connected to the electronic endoscope, and the processed images are displayed on a monitor.

The electronic endoscope thus visualizes the inside of the body cavity of the subject under inspection in real time fashion. The captured images of the interior of the body cavity not only show the whole subject tissues but also individual details of the subject tissues, including fine or capillary vessels, deep blood vessels, pit patterns or gland orifice structures, as well as tissue surface asperities like concavity and convexity. Observing the condition of the subject tissues as the whole and in detail allows making diagnoses as to whether there are any lesions like a tumor.

When the operator of the endoscope detects a lesion from the image of the body cavity, the operator will usually scan the periphery around the detected lesion to search for metastasis of this lesion. For this purpose, the operator moves the distal end of the probing portion up and down or turns the direction of the distal end inside the cavity. However, it sometimes happens that the endoscope loses trace of the initially-detected lesion after the metastatic search in the peripheral area. To prevent this, JPA 2002-095625 suggests detecting a lesion as feature points from endoscopic images and tracing the feature points so as not to lose sight of the lesion.

In the prior art disclosed in JPA 2002-095625, patterns of the feature points of the lesion may be recognized to trace the lesion based on the recognized patterns. However, exact and steady detection of a similar portion to the recognized patterns from newly captured images can be difficult. Accordingly, the target tracing method based on pattern recognition can be less accurate.

The present invention has an object to provide an electronic endoscope system, a processor for an electronic endoscope and a target tracing method, which make it possible to trace a target such as a lesion accurately and steadily even while a doctor or operator is zooming an endoscopic image or moving the distal end of the endoscope in various directions during the imaging.

SUMMARY OF THE INVENTION

In an electronic endoscope system having an imaging device for obtaining image signals through imaging of an interior of a body cavity at constant intervals, and an endoscopic image producing device for producing endoscopic images sequentially based on the image signals, the present invention provides a special light projecting device for projecting special illumination light into the body cavity, the special illumination light having a different wavelength range from white light, a tracing target designating device for designating a tracing target in an endoscopic image, a biological information acquiring device for acquiring biological information on the designated tracing target from image signals obtained while the special illumination light is being projected into the body cavity, and a tracing device for tracing the designated tracing target in endoscopic images captured after the tracing target is designated, on the basis of the biological information acquired by the biological information acquiring device.

The tracing target designating device preferably includes a display device for displaying an area designating frame on endoscopic images on a screen, and a lock-on device for designating a portion confined in the area designating frame as the tracing target.

The biological information acquiring device preferably includes a memory for storing biological information on the tracing target acquired when the tracing target is designated by the tracing target designating device.

Preferably, the biological information acquired by the biological information acquiring device includes vascular information including at least one of blood vessel depth, blood concentration, and oxygen saturation.

In a preferred embodiment, the special light projecting device is adapted to project at least three narrowband rays onto subject tissues including blood vessels in the body cavity. These at least three narrowband rays preferably have different wavelength ranges from each other within a range of 400 nm to 600 nm, including a blue ray band and a green ray band. The biological information acquiring device preferably includes a first narrowband signal obtaining device for obtaining a plurality of narrowband signals corresponding respectively to the narrowband rays from among the image signals obtained by the imaging device, and a first vascular information acquiring device for acquiring vascular information including information on blood vessel depth and blood concentration on the basis of the plurality of narrowband signals.

Preferably, the first narrowband signal obtaining device obtains first and second narrowband signals corresponding to first and second narrowband rays having different wavelength ranges from each other in the blue ray band, and a third narrowband signal corresponding to a third narrowband ray in the green ray band.

Preferably, the first narrowband ray has a wavelength range of 405±10 nm, the second narrowband ray has a wavelength range of 470±10 nm, and the third narrowband ray has a wavelength range of 560±10 nm.

In a preferred embodiment, the special light projecting device is adapted to project a plurality of narrowband rays onto subject tissues including blood vessels in the body cavity. The plurality of narrowband rays preferably have different wavelength ranges from each other, at least one of the different wavelength ranges having a center wavelength of 450 nm or less. The biological information acquiring device preferably includes a second narrowband signal obtaining device for obtaining a plurality of narrowband signals corresponding respectively to the narrowband rays from among the image signals, and a second vascular information acquiring device for acquiring vascular information including information on blood vessel depth and oxygen saturation on the basis of the plurality of narrowband signals.

Preferably, each of the plurality of narrowband rays includes a wavelength, to which oxygenated hemoglobin shows a different degree of light absorbance from reduced hemoglobin, and the plurality of narrowband signals vary differently from each other depending on oxygen saturation of blood.

In another embodiment, the special light projecting device can project an exciting light for causing subject tissues inside the body cavity to generate fluorescent light, and the biological information acquiring device acquires information on the fluorescent light as the biological information through imaging of the generated fluorescent light.

In a further embodiment, the biological information acquiring device acquires pit patterns as the biological information.

According to the present invention, a processor for an electronic endoscope includes a receiving device for receiving image signals that are obtained through imaging of an interior of a body cavity at constant intervals by the electronic endoscope; an endoscopic image producing device for producing endoscopic images sequentially based on the image signals; a tracing target designating device for designating a tracing target in an endoscopic image; a biological information acquiring device for acquiring biological information on the designated tracing target from image signals, which are received while special illumination light having a different wavelength range from white light is being projected into the body cavity; and a tracing device for tracing the designated tracing target in endoscopic images captured after the tracing target is designated, on the basis of the biological information acquired by the biological information acquiring device.

In another aspect of the present invention, a target tracing method comprising the steps of obtaining image signals through imaging of an interior of a body cavity at constant intervals; producing endoscopic images sequentially based on the image signals; designating a tracing target in an endoscopic image; projecting special illumination light into the body cavity, the special illumination light having a different wavelength range from white light; acquiring biological information on the designated tracing target from image signals obtained while the special illumination light is being projected into the body cavity; and tracing, on the basis of the biological information, the designated tracing target in endoscopic images captured after the tracing target is designated.

According to the present invention, a designated target such as a lesion in a body cavity may be traced accurately and steadily on the basis of the biological information on the target that is acquired from image signals obtained at the time of designation of the target, even while the magnification of the endoscopic image is changed or the distal end of the endoscope is turned in various directions during the imaging.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 5A is an explanatory diagram illustrating an endoscope distal end inserted in a body cavity and an image of a body cavity inner wall surface captured by the endoscope in this position;

FIG. 5B is an explanatory diagram illustrating the endoscope distal end inserted deeper in the body cavity and an image of the body cavity inner wall surface captured in this position;

FIG. 6A is an explanatory diagram illustrating a position of the endoscope distal end in the body cavity and an image of the body cavity inner wall surface captured in this position;

FIG. 6B is an explanatory diagram illustrating a position of the endoscope distal end inserted deeper in the body cavity than the position of FIG. 6A and an image of the body cavity inner wall surface captured in this position;

FIG. 13 is a flowchart illustrating the operation of the present invention;

DESCRIPTION OF THE PREFERRED EMBODIMENTS

Figure 1:
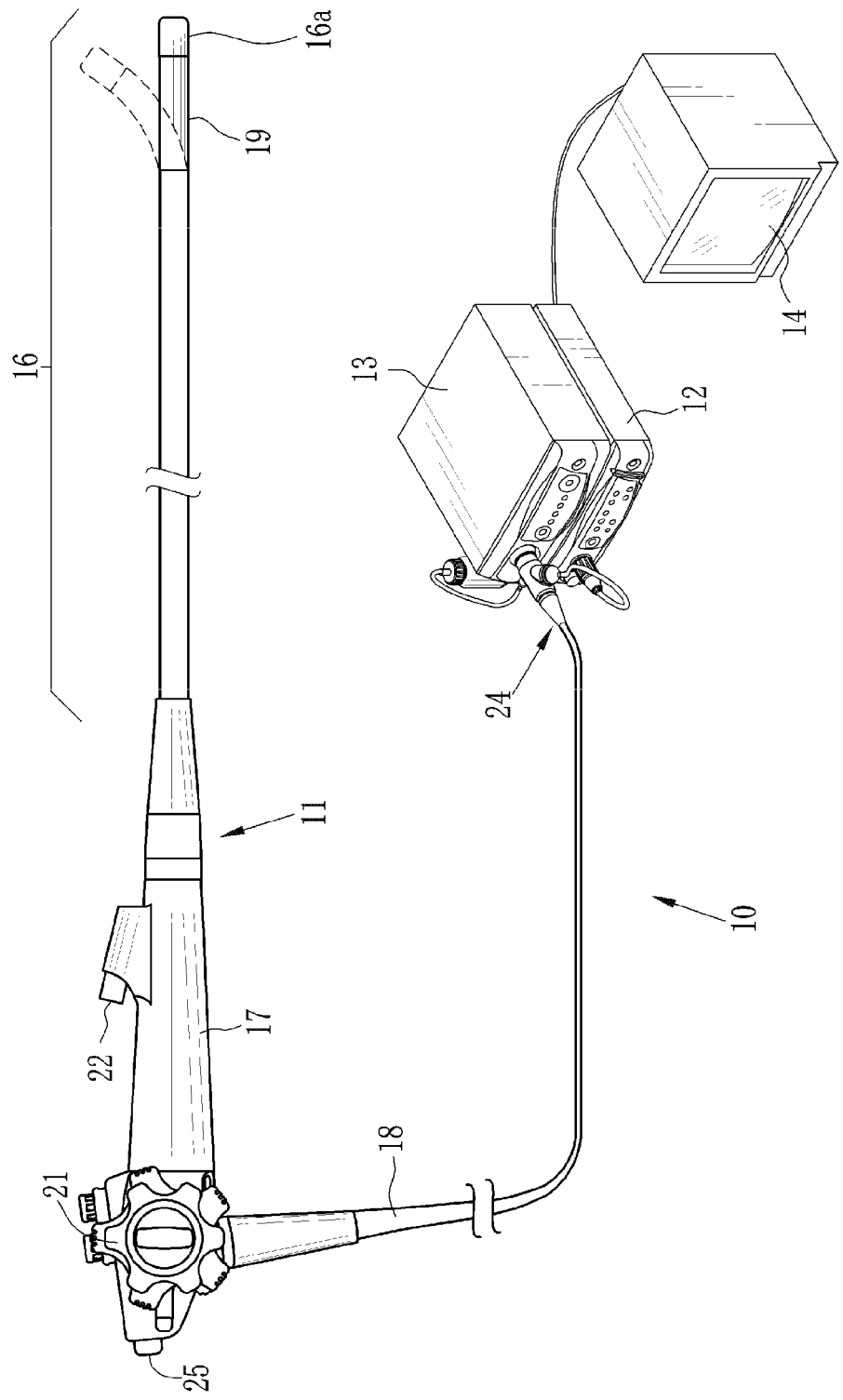
FIG. 1 is a diagram illustrating an outer appearance of an electronic endoscope system.

As shown in FIG. 1, an electronic endoscope system 10 according to the first embodiment of the present invention includes an electronic endoscope 11, a processor 12, a light source unit 13 and a monitor 14. The endoscope 11 images the interior of a body cavity of a subject under inspection. The processor 12 produces images of the tissues inside the body cavity from electronic signals from the endoscope 11. The light source unit 13 provides light for illuminating the inside of the body cavity. The monitor 14 displays the images of the interior of the body cavity. The electronic endoscope 11 includes a flexible probing portion 16 to be inserted into the body cavity, a handling portion 17 coupled to a proximal end of the probing portion 16, and a cord 18 connecting the handling portion 17 to the processor 12 and the light source unit 13.

The probing portion 16 has a curving distal end that consists of serially linked segments. The curving portion 19 may curve in any directions in response to the operation on an angle knob 21 of the handling portion 17. A tip portion 16a formed in the distal end of the curving portion 19 contains an optical system for imaging the interior of the body cavity. The tip portion 16a may be oriented to any desirable direction inside the body cavity through the curving portion 19.

The cord 18 has a connector 24 to be coupled to the processor 12 and the light source unit 13. The connector 24 is a complex connector consisting of a connector terminal for data communication and a connector terminal for light source. Through this connector 24, the electronic endoscope 11 may be removably connected to the processor 12 and the light source unit 13.

Figure 2:
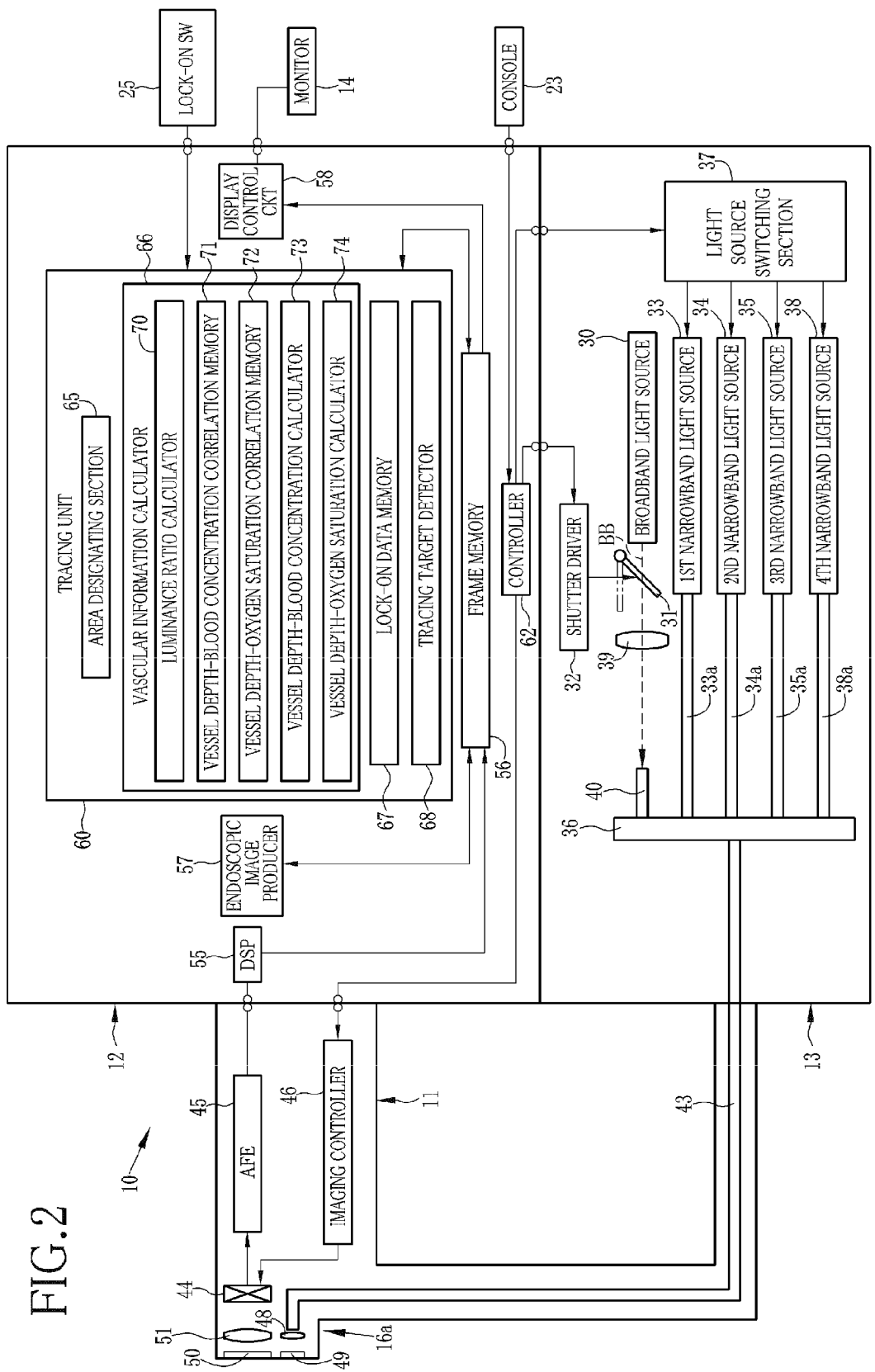
FIG. 2 is a block diagram illustrating the circuitry of an electronic endoscope system, according to a first embodiment of the present invention.

As shown in FIG. 2, the light source unit 13 includes a broadband light source 30, a shutter 31, a shutter driver 32, first to fourth narrowband light sources 33 to 35 and 38, a photo-coupler 36, and a light source switching section 37. The broadband light source 30 may be a xenon lamp, white LED or micro-white light source, which emits broadband light BB having wavelengths ranging from the red ray region to the blue ray region (about 470 nm to 700 nm). The broadband light source 30 is kept ON while the electronic endoscope 11 is in operation. The broadband light BB from the broadband light source 30 is converged through a condenser lens 39 and then introduced into a broadband optical fiber 40.

A shutter 31 is installed in between the broadband light source 30 and the condenser lens 39, to be movable into a light path of the broadband light BB to block the broadband light BB, or out of the light path to allow the broadband light BB to travel to the condenser lens 39. A shutter driver 32 is connected to a controller 62, to control driving the shutter 31 according to instructions from the controller 62. The controller 62 is included in the processor 12.

The first to fourth narrowband light sources 33 to 35 and 38 may be laser diodes or the like. The first to fourth narrowband light sources 33 to 35 and 38 emit first to fourth narrowband rays N1, N2, N3 and N4, respectively. The first narrowband ray N1 is a blue ray of a wavelength limited to 400±10 nm, preferably to 405 nm, the second narrowband ray N2 is a blue ray of a wavelength limited to 470±10 nm, preferably to 473 nm, the third narrowband ray N3 is a green ray of a wavelength limited to 560±10 nm, preferably to 560 nm, and the fourth narrowband rays N4 is a ray of a wavelength limited to 440±10 nm, preferably to 445 nm. The first to fourth narrowband light sources 33 to 35 and 38 are coupled to the first to fourth narrowband optical fibers 33a to 35a and 38a respectively, so that the first to fourth narrowband rays N1 to N4 from the respective light sources are introduced into the first to fourth narrowband optical fibers 33a to 35a and 38a respectively.

The coupler 36 couples the broadband optical fiber 40 and the first to fourth narrowband optical fibers 33a to 35a and 38a to a light guide 43 in the electronic endoscope. Thus, the broadband light BB can enter the light guide 43 via the broadband optical fiber 40. On the other hand, the first to fourth narrowband rays N1 to N4 can enter the light guide 43 through the first to fourth narrowband optical fibers 33a to 35a and 38a respectively.

The light source switching section 37 is connected to the controller 62 in the processor 12, to turn the first to fourth narrowband light sources 33 to 35 and 38ON or OFF according to the instruction from the controller 62. In an ordinary inspection mode, the broadband light source 30 is turned ON to illuminate the inside of body cavity with the broadband light BB to capture a broadband light image, whereas the first to fourth narrowband light sources 33 to 35 and 38 are turned OFF. On the other hand, in a tracing mode for tracing a target, such as a lesion, three kinds of processes will be sequentially executed under different illuminating conditions: tracing target designating process, vascular information acquiring process, and tracing target detecting process.

The tracing target designating process is an initial process for designating a tracing target by locking on the target. In this process, the broadband light BB is projected into the body cavity to capture a broadband light image, and the first to fourth narrowband light sources 33 to 35 and 38 are turned OFF, like in the ordinary inspection mode. After the tracing target is locked on, the vascular information acquiring process is executed to acquire information on blood of the target. When the system 10 is switched to the vascular information acquiring process, the shutter 31 is inserted into the light path of the broadband light BB to block it from the body cavity. When the broadband light BB is blocked, the first narrowband light source 33 is first turned on through the light source switching section 37. Then, while the first narrowband ray N1 is illuminating inside the body cavity, imaging of the subject tissues is carried out. When the imaging is complete, the controller 62 outputs an instruction to switch over the light source, upon which the first narrowband light source 33 is turned OFF, and the second narrowband light source 34 is turned ON. Thereafter when an image has been captured from the body cavity under the illumination of the second narrowband, the second narrowband light source 34 is turned OFF, and the third narrowband light source 35 is turned ON. When another image has been captured under the illumination of the third narrowband ray N3, the third narrowband light source 35 is turned OFF, and the fourth narrowband light source 38 is turned ON. Then another image is captured under the fourth narrowband ray N4 and, thereafter, the fourth narrowband light source 38 is turned OFF.

The vascular information acquiring process is followed by the tracing target detecting process, which is for detecting the locked-on target from the broadband light image as captured in the tracing target designating process. In the tracing target detecting process, the shutter 31 is set out of the light path of the broadband light BB for a certain time, allowing illuminating the interior of the body cavity with the broadband light BB. Thereafter, the shutter 31 is inserted to block the broadband light BB again. Then the first to fourth narrowband light sources 33 to 35 and 38 are sequentially turned ON and OFF to illuminate the interior of the body cavity with the first to fourth narrowband rays N1 to N4, one after another for a certain period each, and an image is captured under each of the first to fourth narrowband rays N1 to N4, like in the vascular information acquiring process.

To capture images from the body cavity, the electronic endoscope 11 includes the light guide 43, a CCD 44, an analog front end (AFE) 45, and an imaging controller 46. The light guide 43 may be a large-diameter optical fiber or a handle fiber, which has an inlet end inserted into the coupler 36 in the light source unit 13. An outlet end of the light guide 43 is opposed to a projection lens 48 that is mounted in the tip portion 16a. The light from the light source unit 13 is conducted through the light guide 43 and then outputs to the projection lens 48. The light entering the projection lens 48 is projected into the body cavity through a lightening window 49 that is mounted in a face end of the tip portion 16a. The broadband light BB and the first to fourth narrowband rays N1 to N4 are individually reflected from the body cavity, and then fall on a condenser lens 51 through an observation window 50 that is mounted in the face end of the tip portion 16a.

The CCD 44 may be a monochrome CCD. The CCD 44 receives the light from the condenser lens 51 on a photo sensing surface 44a, converts the received light to electric charges and accumulates the charges. The accumulated charges are read out as image signals and sent to the AFE 45. Hereinafter, the image signal corresponding to the broadband light BB falling on the CCD 44 will be referred to as a broadband image signal, whereas the image signals corresponding to the narrowband rays N1 to N4 falling on the CCD 44 will be referred to as first to fourth narrowband image signals respectively.

The AFE 45 is constituted of a correlated double sampling circuit (CDS), an automatic gain control circuit (AGC), and an analog-to-digital converter (A/D), which are not shown in the drawings. The CDS processes the image signal from the CCD 44 through correlated double sampling, to eliminate noises that may be caused by the drive of the CCD 44. The AGC amplifies the image signal after the noise reduction through the CDS. The A/D converts the amplified image signal to a digital image signal of a predetermined bit number, and outputs the digital image signal to the processor 12.

Figure 3A:
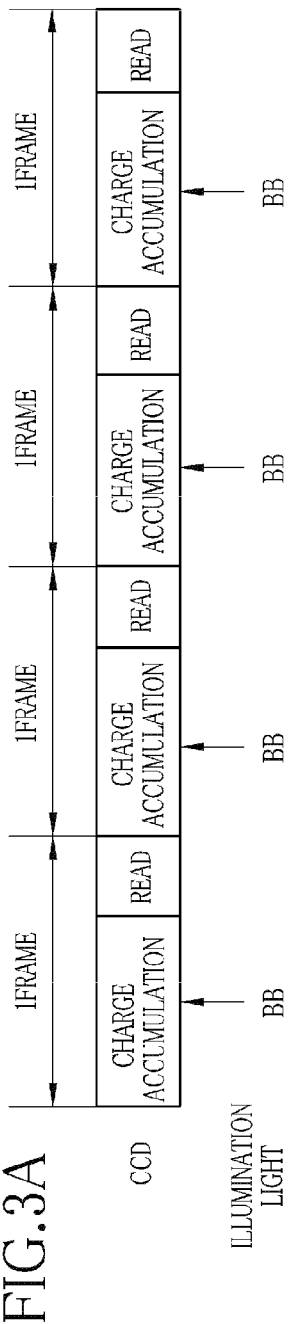
FIG. 3A is an explanatory diagram illustrating an imaging operation of a CCD in an ordinary inspection mode or in a tracing target designating process.

The imaging controller 46 is connected to the controller 62 in the processor 12, to send a drive signal to the CCD 44 in response to a corresponding instruction from the controller 62. Based on the drive signal from the imaging controller 46, the CCD 44 outputs the image signal to the AFE 45 at a designated frame rate. When the system 10 is set at the ordinary inspection mode, as shown in FIG. 3A, two operation steps are carried out during one frame capturing period: the broadband light BB being photo-electrically converted to electric charges and accumulated as the signal charges, and the accumulated signal charges being read as a broadband image signal. The system 10 repeats these operation steps so long as it is set at the ordinary inspection mode.

On the other hand, when the system 10 is switched from the ordinary inspection mode to the tracing mode, the tracing target designating process is executed first. In the tracing target designating process, a broadband image signal is read out during a frame capturing period in the same way as in the ordinary inspection mode as shown in FIG. 3A. This operation is repeated in one frame capturing period after another in the tracing target designating process.

Figure 3B:
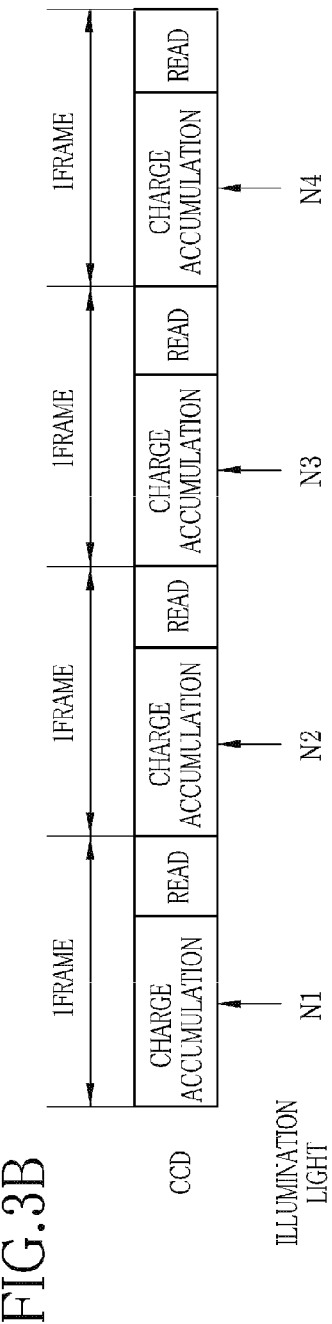
FIG. 3B is an explanatory diagram illustrating an imaging operation of the CCD in a vascular information acquiring process.

When the system 10 switches from the tracing target designating process to the vascular information acquiring process, electric charges obtaining through photo-electric conversion of the first narrowband ray N1 are accumulated as signal charges, and the accumulated signal charges are read out as a first narrowband image signal during a first frame capturing period, as shown in FIG. 3B. After the first narrowband image signal is completely read out, electric charges obtained through photo-electric conversion of the second narrowband ray N2 are accumulated as signal charges, and the accumulated signal charges are readout as a second narrowband image signal in a second frame capturing period.

After the second narrowband image signal is completely read out, electric charges obtained through photo-electric conversion of the third narrowband ray N3 are accumulated as signal charges, and the accumulated signal charges are read out as a third narrowband image signal in a third frame capturing period. Thereafter, electric charges obtained through photo-electric conversion of the fourth narrowband ray N4 are accumulated as signal charges, and the accumulated signal charges are read out as a fourth narrowband image signal in a fourth frame capturing period.

Figure 3C:
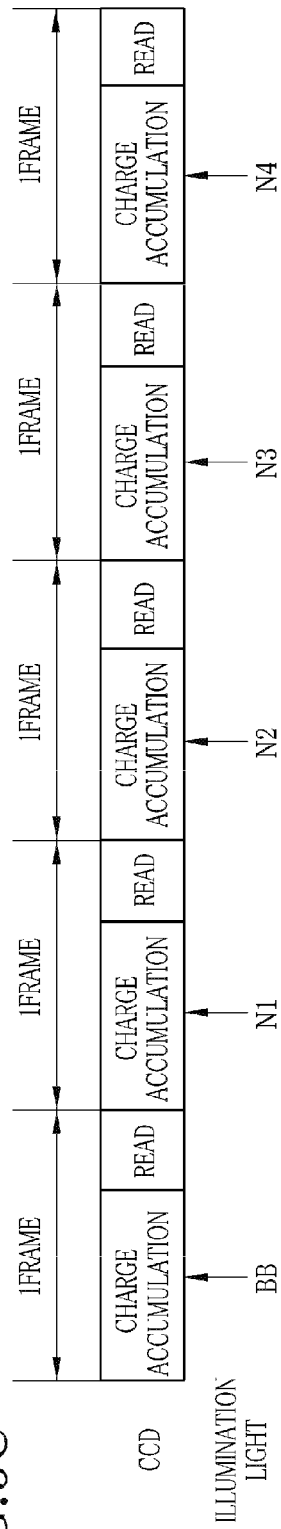
FIG. 3C is an explanatory diagram illustrating an imaging operation of the CCD in a tracing target detecting process.

When the system 10 switches from the vascular information acquiring process to the tracing target detecting process, as shown in FIG. 3C, a broadband image signal is read out in a first frame capturing period in the same way as in the ordinary inspection mode. After the broadband image signal is completely read out, first to fourth narrowband image signals are sequentially read out in the same way as in the vascular information acquiring process. The sequential reading of broadband and narrowband image signals will be repeated so long as the tracing target detecting process continues.

As shown in FIG. 2, the processor 12 includes a digital signal processor (DSP) 55, a frame memory 56, an endoscopic image producer 57, a display control circuit 58, and a tracing unit 60, which are supervised by the controller 62. The DSP 55 processes the broadband image signal and the first to fourth narrowband image signals, as being output from the AFE 45 of the electronic endoscope, for color-separation, color-interpolation, white-balance adjustment, gamma correction and the like, to produce broadband image data and first to fourth narrowband image data. The frame memory 56 stores the broadband image data and the first to fourth narrowband image data as produced by the DSP 55.

The endoscopic image producer 57 produces a broadband light image 63 from the broadband image data stored in the frame memory 56. The display controller 58 controls the monitor 14 to display the broadband light image 63, as shown for example in FIG. 4.

The tracing unit 60 includes an area designating section 65, a vascular information calculator 66, a lock-on data memory 67, and a tracing target detector 68. The area designating section 65 is for setting an area designating frame Ra that is used for designating a tracing target S. The vascular information calculator 66 calculates vascular information of the target S on the basis of the first to fourth narrowband image data. The lock-on data memory 67 stores the vascular information calculated by the vascular information calculator 66. The tracing target detector 68 detects the target S from a broadband light image 64 captured after the designation of the target S, on the basis of the calculated vascular information.

Figure 4:
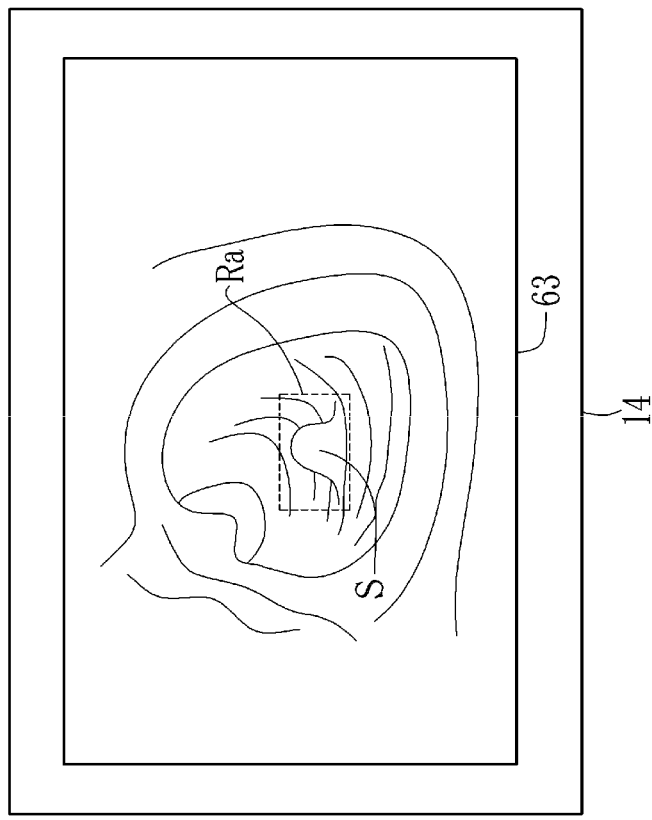
FIG. 4 is a view of an endoscopic image displayed on a monitor.

The area designating section 65 may set up the location and the size of the area designating frame Ra while displaying the area designating frame Ra on the monitor 14. The operator may manipulate the angle knob 21 of the handling portion 17 (see FIG. 1), as is shown in FIG. 4, to confine a target to be traced, such as a lesion, in the area designating frame Ra, while observing the broadband light image 63 on the monitor 14. When a lesion or the like is confined in the area designating frame Ra, the operator pushes the lock-on switch 25 of the handling portion 17. Then, the lesion inside the area designating frame Ra is designated as the tracing target S. This operation may be called "lock-on".

On the basis of the first to fourth narrowband image data, the vascular information calculator 66 determines three kinds of vascular information: vessel depth, blood concentration, and oxygen saturation. Specified configurations of the vascular information calculator 66 will be described in detail later. The lock-on data memory 67 stores the vascular information of the tracing target S, which are calculated by the vascular information calculator 66.

In the broadband light image 64 captured after the lock-on or target designation, the tracing target detector 68 detects an area that has vascular information acquired by the vascular information calculator 66 or stored in the lock-on data memory 67. Thus, the target S is traceable in the broadband light image 64 captured after the lock-on, using the vascular information acquired at the time of lock-on.

For example, as shown in FIG. 5A, when a lesion on a wall surface of a body cavity is locked on as a tracing target S in the broadband light image 63, and vascular information on the locked-on target S indicate that the vessel depth is middle, the blood concentration is high, and the oxygen saturation is low, the tracing target detector 68 detects such an area from the broadband light image 64 captured after the lock-on, of which the vessel depth is middle, the blood concentration is high, and the oxygen saturation is low. If the operator inserts the probing portion 16 deeper into the body cavity after the lock-on operation, and then a broadband light image 64 is captured, as shown in FIG. 5B, the tracing target detector 68 detects an area Rb of which the vessel depth is middle, the blood concentration is high, and the oxygen saturation is low within the broadband light image 64. Thus the target S is traceable.

If, for instance, a small lesion is found at a deeper point inside the body cavity, as shown in FIG. 6A, this lesion may be locked on as a tracing target S, and vascular information on this target S is detected. Then the target S may be traced based on the vascular information on this target S, as shown in FIG. 6B. Therefore, the operator can insert the probing portion 16 deeper into the body cavity and turn the tip portion 16a in appropriate directions without losing trace of the target S. Thus, the operator can instantly put the tip portion 16a closer to the target lesion S.

Figure 7A:
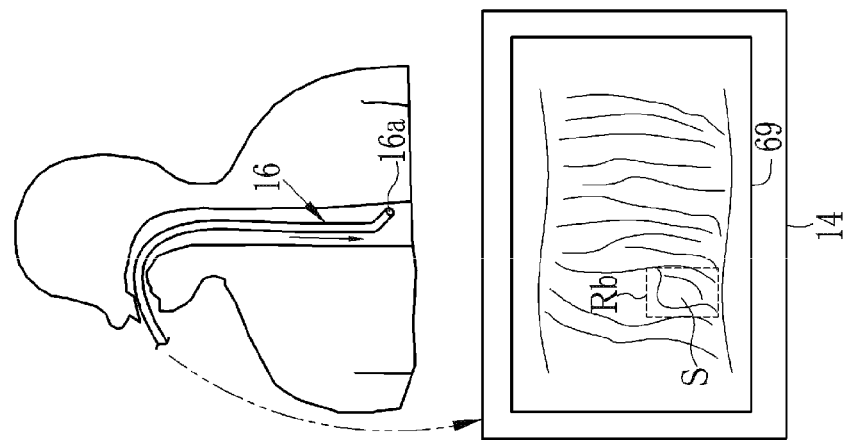
FIG. 7A is an explanatory diagram illustrating a position of the endoscope distal end in the body cavity and an image of the body cavity inner wall surface captured in this position.
Figure 7B:
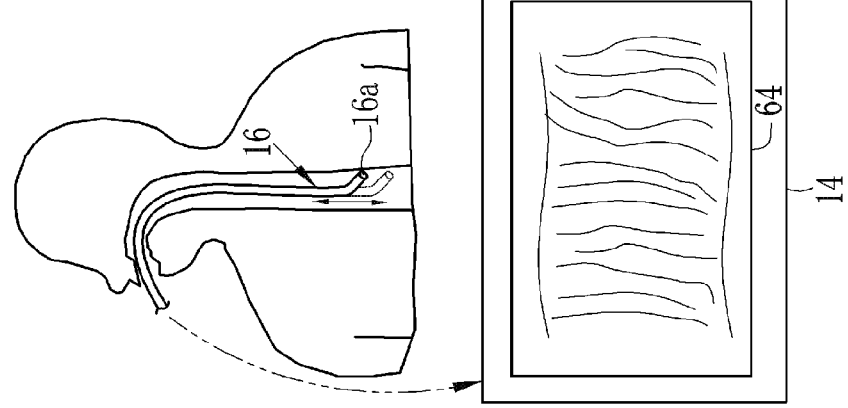
FIG. 7B is an explanatory diagram illustrating a position of the endoscope distal end inserted less deeply in the body cavity than the position of FIG. 7A and an image of the body cavity inner wall surface captured in this position.
Figure 7C:
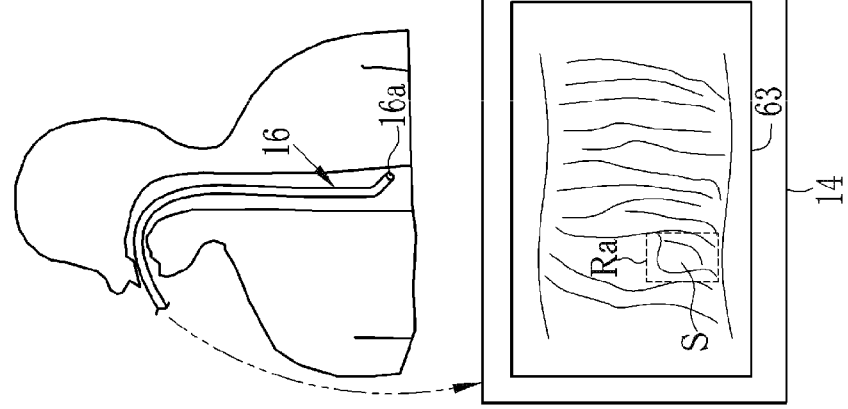
FIG. 7C is an explanatory diagram illustrating a position of the endoscope distal end inserted deeper in the body cavity than the position of FIG. 7B and an image of the body cavity inner wall surface captured in this position.

Moreover, when the operator will search for other lesions or metastases in a peripheral area around a lesion found on the cavity wall, as shown in FIG. 7A, the operator may lock on the initially found lesion as a tracing target S by confining it in the area designating frame Ra. Then vascular information on the target S is acquired and stored in the lock-on data memory 67. Then the operator may move the probing portion 16 or turn the tip portion 16a in appropriate directions inside the body cavity, to check if there are any other lesions or metastases. During this searching, the initially found lesion may disappear from the monitor 14, as shown in FIG. 7B. However, when the operator moves back the probing portion 16 to put the tip portion 16a closer to the initially found lesion and confirm the initially found lesion, the tracing target detector 68 detects from a broadband light image 69 a corresponding area Rb to the area designated by the area designating frame Ra, on the basis of the vascular information stored in the lock-on data memory 67. Thus, the operator can easily trace the initially found lesion.

Referring back to FIG. 2, the vascular information calculator 66 includes a luminance ratio calculator 70, a vessel depth-blood concentration correlation memory 71, a vessel depth-oxygen saturation correlation memory 72, a vessel depth-blood concentration calculator 73, and a vessel depth-oxygen saturation calculator 74. The luminance ratio calculator 70 identifies such image areas that contain blood vessels, hereinafter called the vascular areas, on the basis of the first to fourth narrowband image data stored in the frame memory 56. For example, the vascular areas may be identified from the difference in luminance between blood vessels and other body parts.

The luminance ratio calculator 70 calculates a first luminance ratio S1 (=Log B1/B2) between the first and second narrowband images with respect to individual pixels in the vascular area, wherein B1 represents luminance of one pixel of the first narrowband image, and B2 represents luminance of a corresponding pixel of the second narrowband image, the corresponding pixels representing the same location of the subject. The luminance ratio calculator 70 also calculates a second luminance ratio S2 (=Log G/B2) between the second and third narrowband images, wherein G represents luminance of a corresponding pixel of the third narrowband image, which also represents the same location of the subject as the corresponding pixels of the first and second narrowband images. Moreover, the luminance ratio calculator 70 calculates a third luminance ratio S3 (=B4/B1) between the fourth and first narrowband images, and a fourth luminance ratio S4 (=B2/B1) between the second and first narrowband images, wherein B4 represents luminance of a corresponding pixel of the fourth narrowband image.

The vessel depth-blood concentration correlation memory 71 stores correlation between the first and second luminance ratios S1 and S2, blood concentration in the vessels (hemoglobin index), and blood vessel depth. This correlation may be previously acquired from analyses of an enormous amount of first to third narrowband image data obtained and accumulated through diagnoses and the like.

Figure 8:
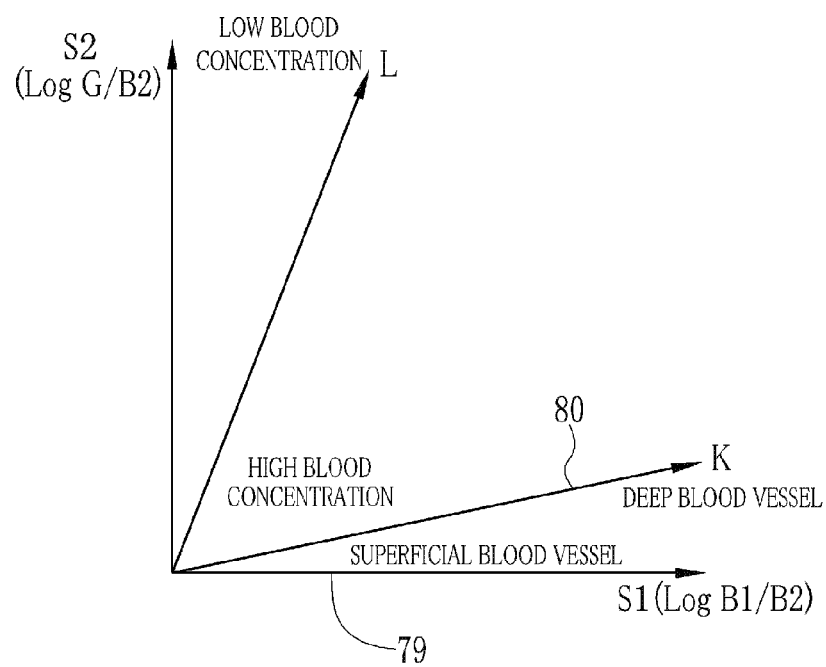
FIG. 8 is a graph showing correlations between first and second luminance ratios S1 and S2, and blood vessel depth and blood concentration.

The vessel depth-blood concentration correlation memory 71 stores the above correlation by correlating two coordinate systems 79 and 80, as shown in FIG. 8: luminance coordinate system 79 representing the first and second luminance ratios S1 and S2, and vascular information coordinate system 80 representing blood concentration and vessel depth. The vascular information coordinate system 80 is provided on the luminance coordinate system 79, and consists of a K-axis representing vessel depth and an L-axis representing blood concentration. The K-axis has a positive gradient to the luminance coordinate system 79 because the vessel depth has a positive correlation with the luminance coordinate system 79. The K-axis slopes upward from left to right and the vessel depth increases from left to right on the K-axis. The L-axis also has a positive gradient to the luminance coordinate system 79 because the vessel depth has a positive correlation with the luminance coordinate system 79. The L-axis slopes upward from left to right and the blood concentration decreases from left to right on the L-axis.

Figure 9:
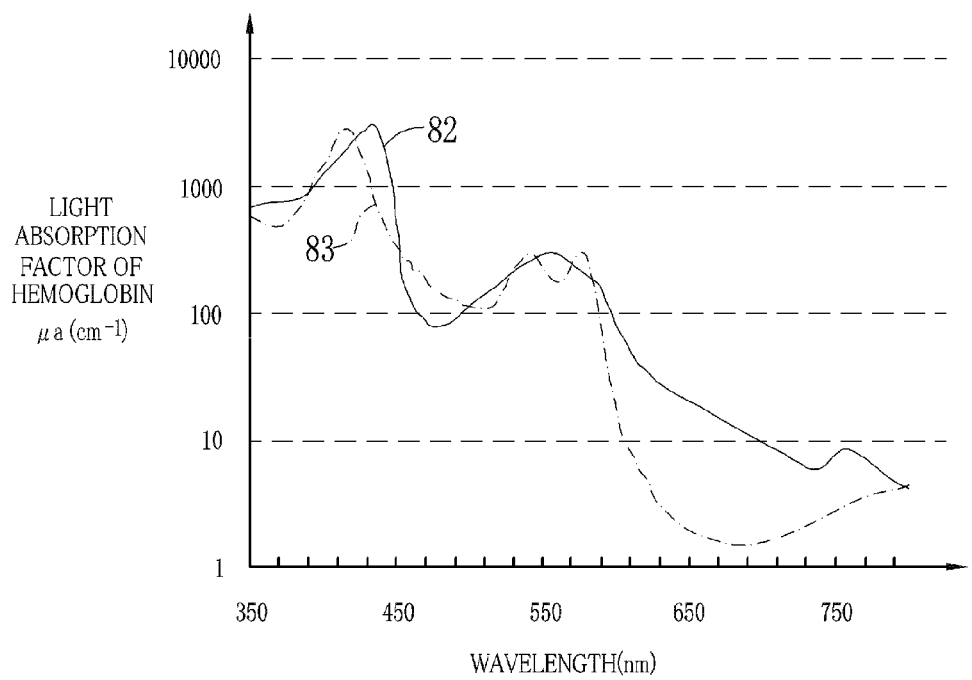
FIG. 9 is a graph showing light absorption coefficients of hemoglobin.

The vessel depth-oxygen saturation correlation memory 72 stores correlation between the third and fourth luminance ratios S3 and S4, the oxygen saturation in the vessels, and the blood vessel depth. This correlation may be previously acquired from analyses of an enormous amount of first, second and fourth narrowband image data obtained and accumulated through diagnoses and the like. As shown in FIG. 9, hemoglobin in the blood vessels has such light absorption characteristics that the light absorption coefficient $\mu a$ varies depending on the wavelength of the illumination light. The light absorption coefficient $\mu a$ indicates the degree of light absorbance of hemoglobin, i.e. the magnitude of light absorption in hemoglobin. The light absorption coefficient is a coefficient used in a formula expressing the attenuation of light projected onto hemoglobin: $Io\exp(-\mu a \times x)$, wherein Io stands for the intensity of light projected from a light source toward a subject tissue, and x(cm) stands for the depth to a blood vessel inside the subject tissue.

As shown in FIG. 9, reduced hemoglobin, which is not combined with oxygen, has a different light absorption characteristic curve 82 from a light absorption characteristic curve 83 of oxygenated hemoglobin that is combined with oxygen. Therefore, the light absorbance of the reduced hemoglobin differs from that of the oxygenated hemoglobin, except at isosbestic points (intersections between the curves 82 and 83), at which reduced hemoglobin and oxygenated hemoglobin have the same degree of light absorbance (the same light absorption coefficient pa). Because of the difference in light absorbance between reduced hemoglobin and oxygenated hemoglobin, the luminance of an identical blood vessel will vary depending upon the percentage of oxygenated hemoglobin in that vessel, even while the vessel is illuminated with light of constant intensity and wavelength. In addition, the light absorption coefficient pa and hence the luminance will change with the wavelength of the illumination light, even while the light intensity is constant.

In view of the above light absorption characteristics of hemoglobin and the facts that the light absorbance of blood vessels will vary depending on the oxygen saturation, especially at wavelengths of 445 nm and 473 nm, and that rays of shorter wavelengths with shorter depths of reach are necessary in order to cover the wide depth range in extracting information about blood vessel depth, the first, second and fourth narrowband rays N1, N2 and N4 should preferably include at least a narrowband ray of a wavelength range having a center wavelength of not more than 450 nm. Moreover, even where the oxygen saturation is the same, if the wavelength of the illumination light is different, the light absorption coefficient will change, and hence the reaching depth of the illumination light into the mucous membrane will change. Accordingly, correlation between luminance ratio and blood vessel depth may be determined making use of the property of light that the depth of reach varies depending on the wavelength.

Figure 10:
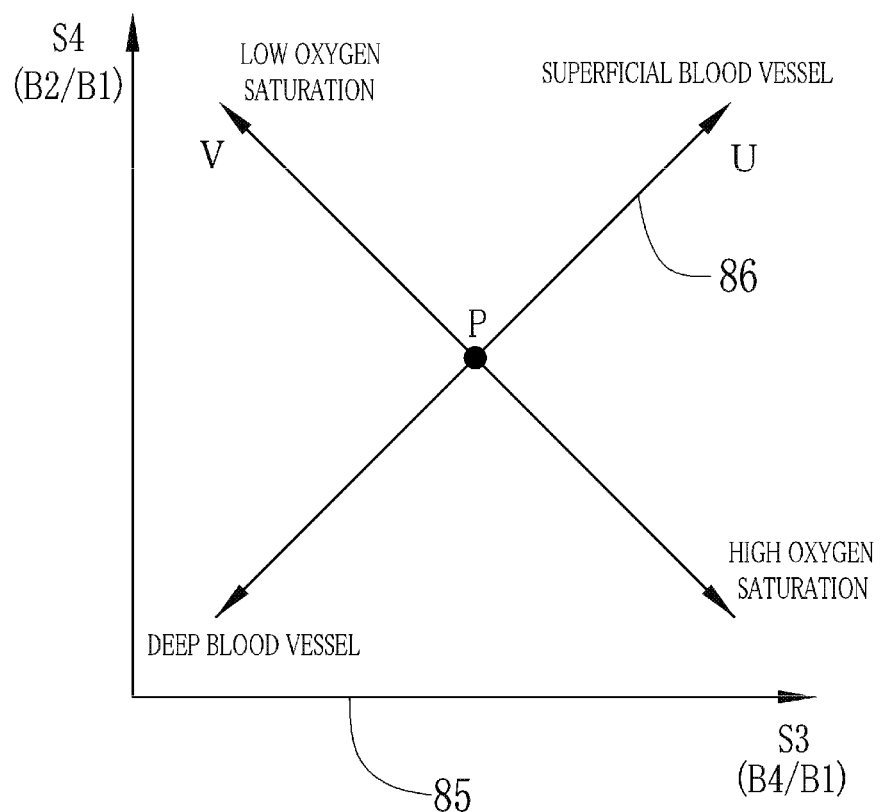
FIG. 10 is a graph showing correlation between third and fourth luminance ratios S3 and S4, and blood vessel depth and oxygen saturation.

The vessel depth-oxygen saturation correlation memory 72 memorizes the correlation between vessel depth and oxygen saturation, as shown in FIG. 10, wherein coordinates of a luminance coordinate system 85 representing the third and fourth luminance ratios S3 and S4 are correlated with coordinates of a vascular information coordinate system 86 representing oxygen saturation and blood vessel depth. The vascular information coordinate system 86 is a U-V coordinate system provided on the luminance coordinate system 85, wherein U-axis represents the blood vessel depth, and V-axis represents the oxygen saturation. The U-axis has a positive inclination because the blood vessel depth has a positive correlation to the luminance coordinate system 85. Concerning the U-axis, upper-right direction indicates decreasing blood vessel depth, and lower-left direction indicates increasing blood vessel depth. On the other hand, the V-axis has a negative inclination because the oxygen saturation has a negative correlation to the luminance coordinate system 85. Concerning the V-axis, upper-left direction indicates descending oxygen saturation, and lower-right direction indicates ascending oxygen saturation.

In the vascular information coordinate system 86, the U-axis and the V-axis orthogonally intersect at a point P. This is because the light absorbance to the fourth narrowband ray N4 has a reversed relation in magnitude to the light absorbance to the second narrowband ray N2. Specifically, as shown in FIG. 9, to the fourth narrowband ray N4 having the wavelength of 440±10 nm, the light absorption coefficient of reduced hemoglobin 82 is higher than the light absorption coefficient of oxygenated hemoglobin 83 having higher oxygen saturation than reduced hemoglobin. On the contrary, to the second narrowband ray N2 having the wavelength of 470±10 nm, the light absorption coefficient of oxygenated hemoglobin 83 is higher than the light absorption coefficient of reduced hemoglobin 82. The order in magnitude of the light absorption coefficient to the fourth narrowband ray N4 and the light absorption coefficient to the second narrowband ray N2 is reversed between the reduced hemoglobin 82 and the oxygenated hemoglobin 83. It is to be noted that the U-axis and V-axis would not be orthogonal if a ray of a wavelength range to which the magnitude relation in the light absorption coefficient is not reversed is used instead of the first, second and fourth narrowband rays N1, N2 and N4. Meanwhile, to the first narrowband ray N1 having the wavelength of 400±10 nm, the light absorption coefficient of oxygenated hemoglobin is approximately equal to that of reduced hemoglobin.

Figure 11A:
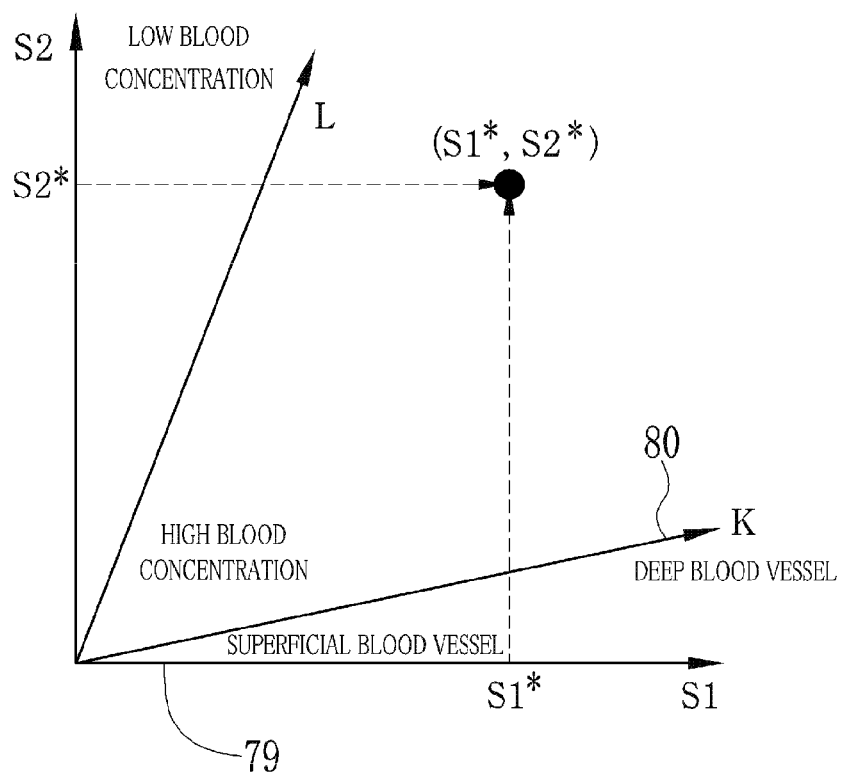
FIG. 11A is an explanatory diagram illustrating a method of determining coordinates (S1*, S2*) of the first and second luminance ratios in a luminance coordinate system.
Figure 11B:
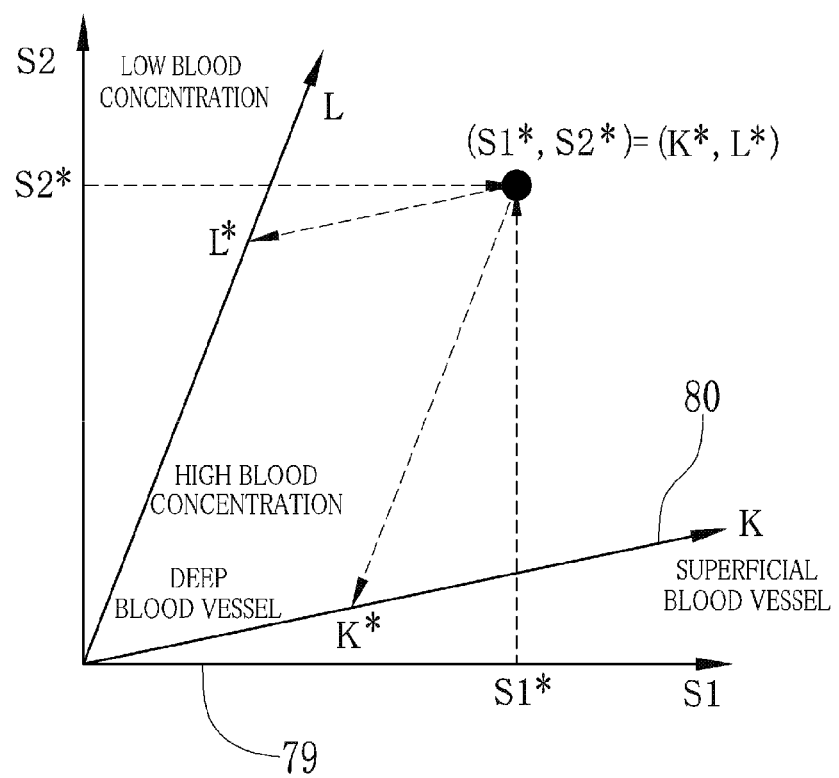
FIG. 11B is an explanatory diagram illustrating a method of determining those coordinates (K*, L*) in a vascular information coordinate system, corresponding to the coordinates (S1*, S2*)

The vessel depth-blood concentration calculator 73 determines coordinates (S1*, S2*) in the luminance coordinate system 79, as shown in FIG. 11A, these coordinates corresponding to the first and second luminance ratios S1* and S2* at a measured point. After determining the coordinates (S1*, S2*), the calculator 73 determines coordinates (K*, L*) in the vascular information coordinate system 80, corresponding to the coordinates (S1*, S2*), as shown in FIG. 11B. Thus, the blood vessel depth K* and the blood concentration L* are determined with respect to a particular pixel in the vascular area.

Figure 12A:
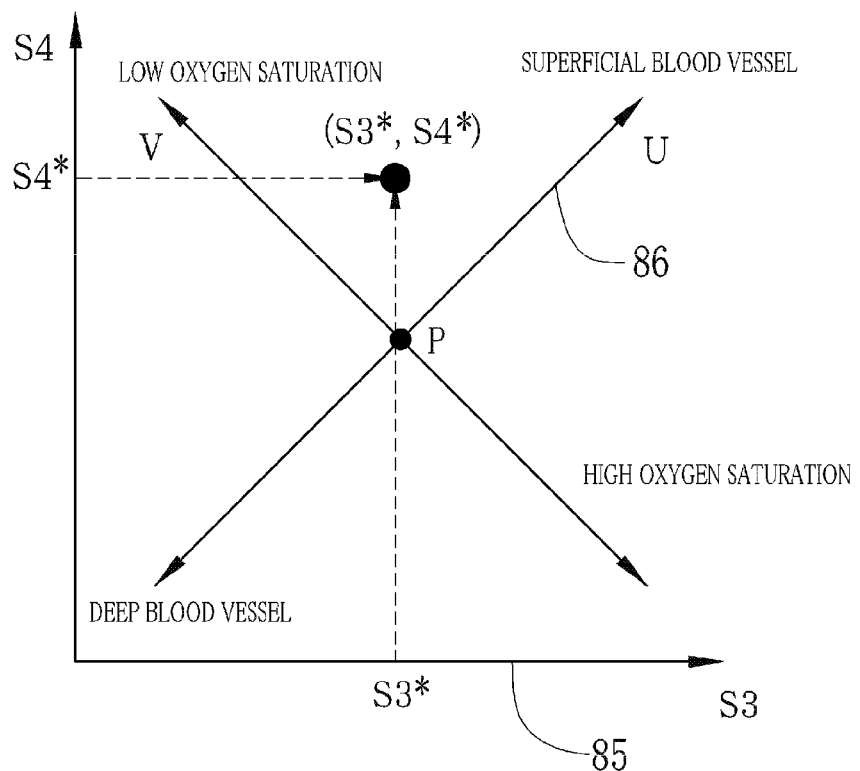
FIG. 12A is an explanatory diagram illustrating a method of determining coordinates (S3*, S4*) of the third and fourth luminance ratios in a luminance coordinate system.
Figure 12B:
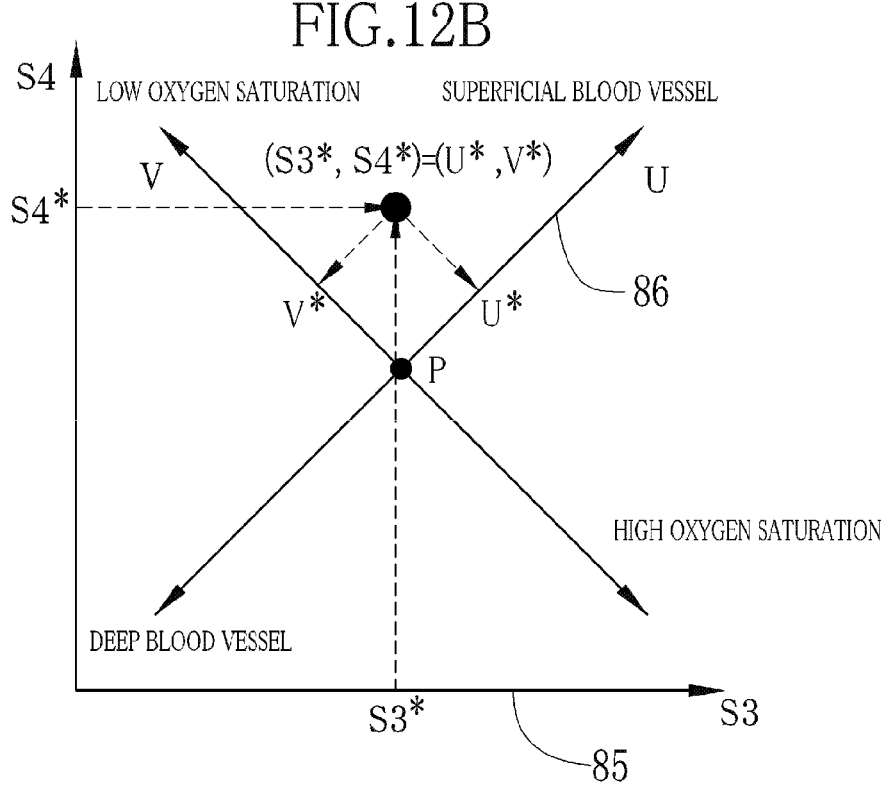
FIG. 12B is an explanatory diagram illustrating a method of determining coordinates (U*, V*) in a vascular information coordinate system, corresponding to the coordinates (S3*, S4*)

The vessel depth-oxygen saturation calculator 74 determines coordinates (S3*, S4*) in the luminance coordinate system 85, as shown in FIG. 12A, these coordinates corresponding to the third and fourth luminance ratios S3* and S4* at a measured point. After determining the coordinates (S3*, S4*), the calculator 74 determines coordinates (U*, V*) in the vascular information coordinate system 86, corresponding to the coordinates (S3*, S4*), as shown in FIG. 12B. Thus, the blood vessel depth U* and the oxygen saturation V* are determined with respect to a particular pixel in the vascular area.

Now the operation of the present invention will be described with reference to the flowchart shown in FIG. 13. First, the console 23 is operated to switch the electronic endoscope system 10 from the ordinary inspection mode to the tracing mode. When the system 10 is switched to the tracing mode, the area designating frame Ra is displayed on the monitor 14. In the tracing target designating process, the broadband light BB is projected into the body cavity to capture broadband light images 63. The operator manipulates the handling portion 17 of the endoscope 11 to move the probing portion 16 inside the body cavity or turn the tip portion 16a in appropriate directions till a tracing target S like a lesion is found in the image 63 and located in the area designating frame Ra. When the target S is located in the area designating frame Ra, the operator pushes on the lock-on switch 25.

When the lock-on switch 25 is pushed on, the system 10 proceeds to the vascular information acquiring process. In the vascular information acquiring process, the shutter driver 32 is activated to insert the shutter 31 into the light path of the broadband light BB, to block it from the body cavity. Then, the first to fourth narrowband light sources 33 to 35 and 38 are sequentially turned ON for a constant period each, to project the first to fourth narrowband rays N1 to N4 successively for the constant period into the body cavity OFF. Under the successive illumination of the first to fourth narrowband rays N1 to N4, the first to fourth narrowband image signals are captured successively. These image signals are sent to the DSP 55 via the AFE 45. The DSP 55 produces the first to fourth narrowband image data from the first to fourth narrowband image signals. The produced first to fourth narrowband image data are stored in the frame memory 56.

Based on the first to fourth narrowband image data stored in the frame memory 56, the vascular information calculator 66 calculates vascular information on the tracing target S, including vessel depth, blood concentration, and oxygen saturation of the target S. The calculated vascular information on the target S is stored in the lock-on data memory 67. Then the vascular information acquiring process is automatically terminated to proceed to the tracing target detecting process.

In the tracing target detecting process, the shutter 31 and the first to fourth narrowband light sources 33 to 35 and 38 are sequentially and cyclically driven to illuminate the interior of the body cavity with the broadband light BB, and then with the first to fourth narrowband rays N1 to N4, one after another for a certain period each. Thus, after the lock-on, broadband image data and first to fourth narrowband image data are periodically obtained at constant intervals. The monitor 14 displays the broadband light image 64 as captured after the lock-on.

Also in the tracing target designating process, on the basis of the obtained first to fourth narrowband image data, the vascular information calculator 66 calculates vascular information on the whole area of the body cavity included in the broadband light image 64 captured after the lock-on target. The tracing target detector 68 determines whether the broadband light image 64 contains an area Rb that has the same vascular information as those stored in the lock-on data memory 67. If there is, the area Rb corresponding to the locked-on target S is indicated by a frame on the broadband light image 64. Thus the target S designated by the lock-on becomes traceable. The same operation as above will be repeated to continue tracing the target S unless the system 10 is switched from the tracing mode to the ordinary inspection mode. When the system 10 is switched to the ordinary inspection mode, the tracing of the target S is terminated.

On the other hand, if the broadband light image 64 does not contain any area Rb that has the same vascular information as those stored in the lock-on data memory 67, the same operation as described so far will be repeated until the tracing target S is detected.

Figure 14:
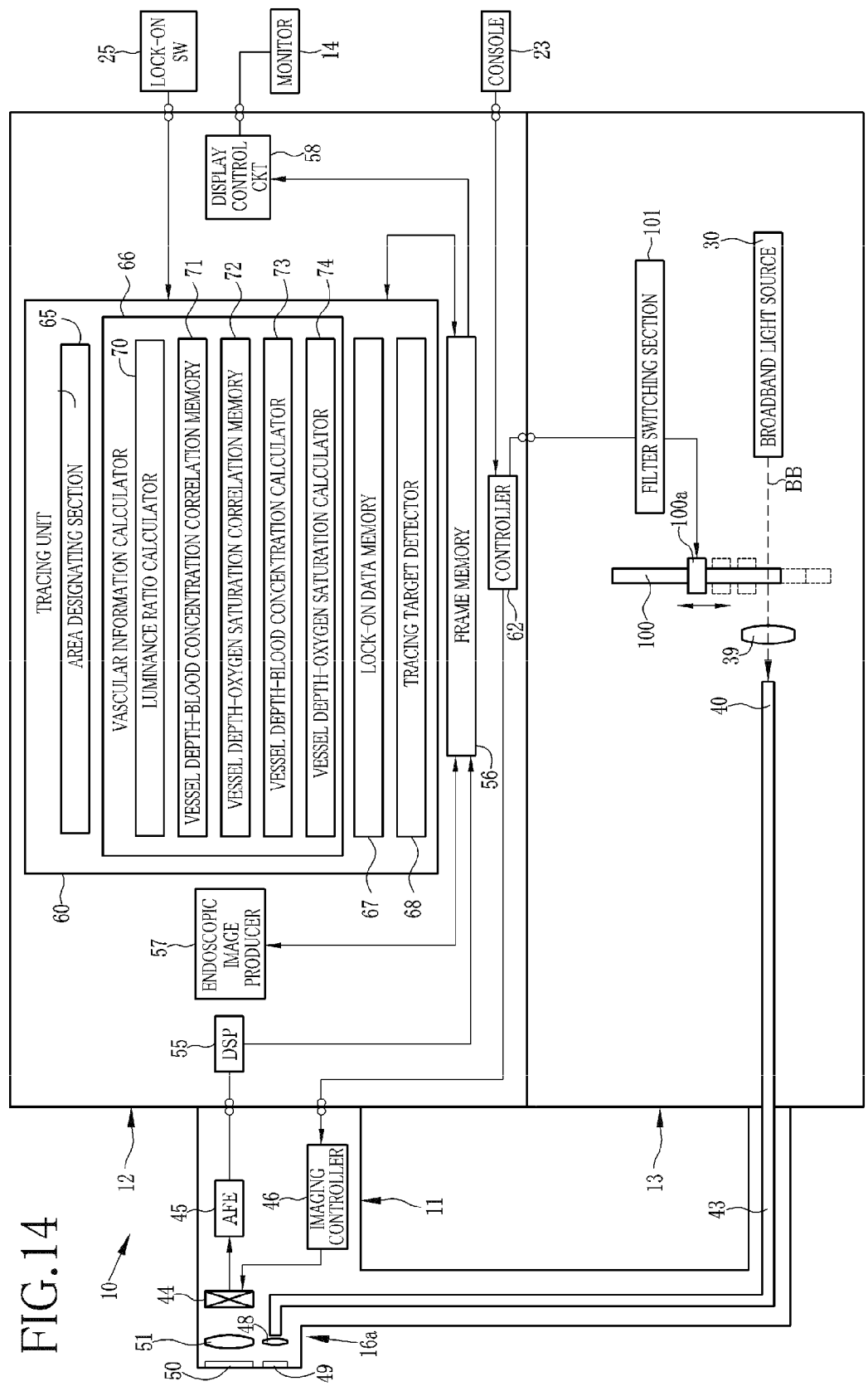
FIG. 14 is a block diagram illustrating the circuitry of an electronic endoscope system according to another embodiment of the present invention.

In the above embodiment, the first to fourth narrowband light sources are used in addition to the broadband light source, for generating the first to fourth narrowband rays N1 to N4 in addition to the broadband light BB. In another embodiment, as shown in FIG. 14, the first to fourth narrowband light sources are not installed, but a rotary filter 100 is installed in between a broadband light source 30 and a condenser lens 39. The rotary filter 100 can rotate about a rotary axis 100a at a constant speed. The rotary filter 100 is also movable in its diagonal direction through a filter switching section 101 that is coupled to the rotary axis 100a.

Figure 15:
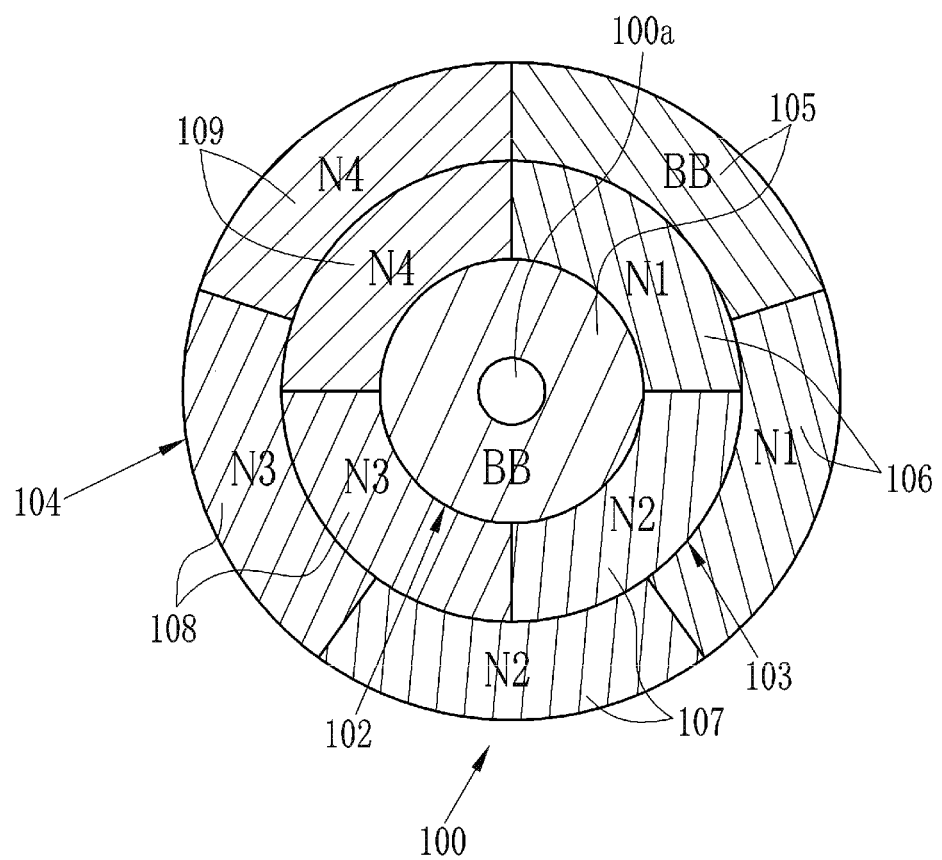
FIG. 15 is a schematic diagram illustrating a rotary filter used in the electronic endoscope system of FIG. 14.

As shown in FIG. 15, the rotary filter 100 includes three coaxial circular zones 102, 103 and 104. The first zone 102 is for passing those light components of the broadband light BB which are used in the ordinary inspection mode and in the tracing target designating process in the tracing mode. The second zone 103 is for passing those light components of the broadband light BB which are used in the vascular information acquiring process. The third zone 104 is for passing those light components of the broadband light BB which are used in the tracing target detecting process. Synchronously with the switching between these modes and processes, the filter switching section 101 moves the rotary filter 100 in the diagonal direction to set a suitable one of these zones 102 to 104 in the light path of the broadband light BB according to the expecting mode and process.

The first zone 102 includes a broadband light permeable sector 105 that allows the whole broadband light BB to pass through it. The second zone 103 includes first to fourth narrowband light permeable sectors 106, 107, 108 and 109. The first narrowband light permeable sector 106 allows the first narrowband ray N1 only to pass through it among the light components of the broadband light BB. The second narrowband light permeable sector 107 allows only the second narrowband ray N2 of the broadband light BB to pass through it. The third or the fourth narrowband light permeable sector 108 or 109 allows only the third or the fourth narrowband ray N3 or N4 to pass through it, respectively. These sectors 106 to 109 are arranged in this order in the circumferential direction. The third zone 104 includes a broadband light permeable sector 105 and first to fourth narrowband light permeable sectors 106 to 109 arranged in this order in the circumferential direction.

The rotary filter 100 is rotatable to place the broadband light permeable sector 105 in the light path of the broadband light source 30 to provide the broadband light BB, or the first, the second, the third or the fourth narrowband light permeable sector 106, 107, 108 or 109 in the light path of the broadband light source 30 to provide the first to fourth narrowband rays N1 to N4 one after another.

It is to be noted that the electronic endoscope system of the present invention may trace multiple targets although the above embodiments have been described with respect to those cases where a single tracing target is designated. When multiple targets are designated, vascular information on these targets should be individually acquired and stored in a memory. In the above embodiment, the vascular information used for tracing includes vessel depth, blood concentration, and oxygen saturation. However, the tracing may be executed based on at least one of these factors.

Although a target is traced using vascular information on this target in the above embodiment, the tracing may be executed based on other biological information on the target than the vascular information, e.g. pit patterns, vessel structures, and/or vessel diameters. Instead of blood vessels, such body parts that contain autofluorescent components, such as collagen, NADH, and FAD, may serve as the tracing target among subject tissues inside the body cavity. In that case, the tracing target containing an autofluorescent component is illuminated with an exciting light, e.g. a narrowband ray of 405 nm, to generate intrinsic fluorescence. Light intensity or other information on the generated intrinsic fluorescence is used for the tracing process. Moreover, it is possible to inject an oncotropic photo-sensitive substance or fluorescent agent, such as porphyrin derivatives, into a patient and project an exciting light, e.g. a narrowband ray of 405 nm, onto a body site that might be affected by a tumor. Since the fluorescent agent accumulated in the tumor generates fluorescence then, the light intensity or other information on the generated fluorescence may be used for tracing the tumor as a target.

In the tracing target detecting process in the above embodiment, vascular information is acquired from the whole body cavity area contained in a broadband light image that is captured after the lock-on operation. If, however, the location of the target in the broadband light image is predictable to some extent, vascular information may be acquired from a limited area where the target is expected to exist. In another alternative embodiment, the area designating frame is not initially displayed on the monitor at the start of the tracing mode, but the area designating frame is displayed to surround a target like a lesion upon designating the target with a pointer using the mouse or console.

The present invention is not only applicable to an electronic endoscope having a probing portion introduced into the body cavity, but also to a capsule type electronic endoscope having an imaging device like a CCD and other components integrated into a capsule.

It should be understood that the present invention is not to be limited to the above embodiments, but many variations and modifications of the present invention will be possible for those skilled in the art without departing from the scope of the present invention as specified in the appended claims.

What is claimed is:

1. An electronic endoscope system comprising:
   an imaging device for obtaining image signals through imaging of an interior of a body cavity at constant intervals;
   an endoscopic image producing device for producing endoscopic images sequentially based on the image signals;
   a special light projecting device for projecting special illumination light into the body cavity, said special illumination light having a different wavelength range from white light;
   a tracing target designating device for designating a tracing target in an endoscopic image;
   a biological information acquiring device for acquiring biological information on the designated tracing target from image signals obtained while said special illumination light is being projected into the body cavity; and
   a tracing device for tracing the designated tracing target in endoscopic images captured after the tracing target is designated, on the basis of the biological information acquired by said biological information acquiring device
   wherein said tracing target designating device comprises:
   a display device for displaying an area designating frame on endoscopic images on a screen; and
   a lock-on device for allowing a user to designate a portion confined in the area designating frame on said screen as the tracing target.

2. The electronic endoscope system as recited in claim 1, wherein said biological information acquiring device comprises a memory for storing biological information on the tracing target acquired when the tracing target is designated by said tracing target designating device.

3. The electronic endoscope system as recited in claim 1, wherein the biological information acquired by said biological information acquiring device includes vascular information including at least one of blood vessel depth, blood concentration, and oxygen saturation.

4. The electronic endoscope system as recited in claim 3, wherein said special light projecting device is adapted to project at least three narrowband rays onto subject tissues including blood vessels in the body cavity, said at least three narrowband rays having different wavelength ranges from each other within a range of 400 nm to 600 nm, including a blue ray band and a green ray band, and wherein
   said biological information acquiring device comprises a first narrowband signal obtaining device for obtaining a plurality of narrowband signals corresponding respectively to the narrowband rays from among the image signals obtained by said imaging device, and a first vascular information acquiring device for acquiring vascular information including information on blood vessel depth and blood concentration on the basis of said plurality of narrowband signals.

5. The electronic endoscope system as recited in claim 4, wherein said first narrowband signal obtaining device obtains first and second narrowband signals corresponding to first and second narrowband rays having different wavelength ranges from each other in the blue ray band, and a third narrowband signal corresponding to a third narrowband ray in the green ray band.

6. The electronic endoscope system as recited in claim 5, wherein the first narrowband ray has a wavelength range of 405±10 nm, the second narrowband ray has a wavelength range of 470±10 nm, and the third narrowband ray has a wavelength range of 560±10 nm.

7. The electronic endoscope system as recited in claim 3, wherein said special light projecting device is adapted to project a plurality of narrowband rays onto subject tissues including blood vessels in the body cavity, said plurality of narrowband rays having different wavelength ranges from each other, at least one of the different wavelength ranges having a center wavelength of 450 nm or less, and wherein
   said biological information acquiring device comprises a second narrowband signal obtaining device for obtaining a plurality of narrowband signals corresponding respectively to the narrowband rays from among the image signals, and a second vascular information acquiring device for acquiring vascular information including information on blood vessel depth and oxygen saturation on the basis of said plurality of narrowband signals.

8. The electronic endoscope system as recited in claim 7, wherein each of said plurality of narrowband rays includes a wavelength, to which oxygenated hemoglobin shows a different degree of light absorbance from reduced hemoglobin, and said plurality of narrowband signals vary differently from each other depending on oxygen saturation of blood.

9. The electronic endoscope system as recited in claim 1, wherein said special light projecting device can project an exciting light for causing subject tissues inside the body cavity to generate fluorescent light, and said biological information acquiring device acquires information on the fluorescent light as the biological information through imaging of the generated fluorescent light.

10. The electronic endoscope system as recited in claim 1, wherein said biological information acquiring device acquires pit patterns as the biological information.

11. A processor for an electronic endoscope, comprising:
    a receiving device for receiving image signals that are obtained through imaging of an interior of a body cavity at constant intervals by said electronic endoscope;
    an endoscopic image producing device for producing endoscopic images sequentially based on the image signals;
    a tracing target designating device for designating a tracing target in an endoscopic image;
    a biological information acquiring device for acquiring biological information on the designated tracing target from image signals, which are received while special illumination light having a different wavelength range from white light is being projected into the body cavity; and
    a tracing device for tracing the designated tracing target in endoscopic images captured after the tracing target is designated, on the basis of the biological information acquired by said biological information acquiring device
    wherein said tracing target designating device comprises:
    a display device for displaying an area designating frame on endoscopic images on a screen; and a lock-on device for allowing a user to designate a portion confined in the area designating frame on said screen as the tracing target.

12. A tracing method comprising the steps of:

obtaining image signals through imaging of an interior of a body cavity at constant intervals;

producing endoscopic images sequentially based on the image signals;

designating a tracing target in an endoscopic image;

projecting special illumination light into the body cavity, said special illumination light having a different wavelength range from white light;

acquiring biological information on the designated tracing target from image signals obtained while said special illumination light is being projected into the body cavity;

tracing, on the basis of the biological information, the designated tracing target in endoscopic images captured after the tracing target is designated;

displaying an area designating frame on endoscopic images on a screen; and designating by a user a portion confined in the area designating frame on said screen as the tracing target.

* * * * *